United States Patent
Parra

[11] Patent Number: 5,146,208
[45] Date of Patent: Sep. 8, 1992

[54] METHOD AND APPARATUS FOR DETECTING INTRUSION INTO A BODY OF WATER

[76] Inventor: Jorge M. Parra, 7332 Grand Blvd., New Port Richey, Fla. 34652

[21] Appl. No.: 675,199

[22] Filed: Mar. 26, 1991

Related U.S. Application Data

[63] Continuation-in-part of Ser. No. 569,121, Aug. 17, 1990, Pat. No. 5,031,637.

[51] Int. Cl.$^5$ .............................................. G08B 13/00
[52] U.S. Cl. ..................................... 340/573; 340/566
[58] Field of Search ................. 340/566, 565, 573; 367/197, 198, 199, 93, 94

[56] References Cited

U.S. PATENT DOCUMENTS

| | | | |
|---|---|---|---|
| 3,867,711 | 2/1975 | Ruscus | 340/566 |
| 4,604,610 | 8/1986 | Baker et al. | 340/566 |
| 4,604,735 | 8/1956 | Parsons | 367/93 |
| 4,890,265 | 12/1989 | Goldstein | 340/566 |
| 4,979,153 | 12/1990 | Terry | 367/93 |

FOREIGN PATENT DOCUMENTS 2755150 6/1975 Fed. Rep. of Germany ........ 340/65

Primary Examiner—Ruth S. Smith
Assistant Examiner—Robert L. Nasser, Jr.
Attorney, Agent, or Firm—Jim Zegeer

[57] ABSTRACT

Noises made by the flow of blood in the human cardiovascular system, respiratory and skeletal noises made in the joints of a skeletal animal provide a wide variety of sounds which, when the human body is partially or completely immersed in a body of acoustically transmissive liquid, are directly coupled to the acoustically transmitted liquid and thus launched into acoustically transmitted liquid. The cardiovascular system has a unique acoustic signature. Joints, for example, which are injured or diseased have unique acoustic signatures e.g., sound they make, which are launched into the water and thus each individual's skeletal system make or produce a unique pattern of noise or sounds which are normally inaudible, but when immersed in a body of water can be detected by hydrophones or underwater microphones. The invention has use in locating missing or lost divers, surveillance of bodies of water for serepititous entry thereto for safe-guarding swimming pools, etc.

8 Claims, 6 Drawing Sheets

METHOD AND APPARATUS FOR DETECTING INTRUSION INTO A BODY OF WATER

REFERENCE TO RELATED APPLICATIONS

This application is a continuation-in-part of my application Ser. No. 07/569,121 for "NON-INVASIVE DIAGNOSTIC METHOD AND APPARATUS" file' Aug. 17, 1990, now U.S Pat. No. 5,031,637.

BACKGROUND AND BRIEF DESCRIPTION OF THE INVENTION

Stethoscopes and like apparatus have been used for many years to listen to sounds made by the human body and to make diagnostic analysis of various conditions in the human body. The sounds produced are typically in the sonic range and while stethoscopes are, obviously, widely used by the medical profession, the types of analysis and uses for such apparatus is relatively limited primarily to the chest cavity area (e.g., breathing and gas flow in the lungs, etc.) and for blood pressure readings in the cardiovascular system.

My patent application Ser. No. 07/569,121 discloses a non-invasive diagnostic apparatus and method wherein the human body or a portion thereof is placed in a body of an acoustically transmissive fluid, such body of acoustically transmitting fluid being contained in a container preferably having sidewalls formed of or coated with acoustically absorbent material. One or more hydrophones are located in the body of fluid to detect or "listen" to sounds, such as cardiovascular sounds, gas flow and skeletal sounds made by body movements. These sounds are passed through a preamplifier, a bandpass filter and discriminator, the function of which may be performed by microprocessors, to a recorder and/or display device. The recorder can record body sounds much in the fashion of an strip chart recorder used for EKG and/or EEG. Typical pool water with chlorine, or salt water, or oils, such as vegetable oils can be used for the acoustically transmissive medium. In addition to audible sounds, the method and apparatus are particularly useful for listening to infrasonic or subsonic sounds. The subject is placed or immersed in the body of acoustically transmissive liquid in a container having acoustically absorbing walls so that there are no unwanted reflections of sounds launched in the water from the human body reflecting off of the walls. One or more hydrophones located in the body of water are used to detect the sonic energy launched by the human body. The human in the body of acoustic liquid is instructed to go through a particular sequence of movement, for example, the arms, (flexion, extension, abduction, adduction), or the back, or legs (inversion eversion), etc. and record is made of the sounds emitted during each of the movements of the specific body parts or the specific movement made by a given patient. For example, an athlete may be asked to bend his or her knee (flexion, extension), elbow (flexion, extension) and the like and a record is made of the sounds generated and launched into the acoustically transmissive liquid. Similar recordings are made for a large number of individuals to provide a norm of the movements of a particular body part in a particular direction and/or at a particular rate of speed. These records then form a database which may be stored in the computer database and used to detect departures from the normal sounds made and thereby provide the physician with a greater body of knowledge to enable successful treatment for the patient.

As noted above, the human acoustic signature is comprised of three main sound groups: Respiratory, Cardiovascular and Musculo-skeletal. When these sounds are analyzed in a liquid medium (e.g., seawater or lake or river water), shared by other living creatures like fish, mollusks, small mammals, crustaceans, etc., any respiratory sound analysis is affected by a large variety of extraneous sounds, such as fish swimming bladders and other hissing sounds. In addition, any musculo-skeletal sounds are diminished significantly if the subject diver is not moving or is moving extremely slowly.

However, the human cardiovascular system signature is strong. It is involuntary and cannot be suppressed, and is easily distinguished from sounds produced by any sea creatures, even sea mammals and fish.

The invention detects the presence, direction and proximity of a human being in or under water regardless of the type of breathing apparatus or swimming method. And, after comparing the incoming signal with the sonic profile of human cardiovascular sound, recorded digitally on the ROM, it can proceed to sound a warning to alert the operator. This system does not require operator interpretation of the received signal, though the signal can be displayed on a screen if desired.

The sound created by the air passage on a scuba regulator is in the same frequency band (32 khz) as that of fish when they transfer gas from one bladder to another, rendering the respiratory system sounds unreliable and open to possible error in operator interpretation. Thus, the filter associated with the cardiovascular channel excludes this band (respiratory system sounds) from the cardiovascular sound channel. This system can be used in a pool or body of water as surveillance against accidental or unauthorized intrusion.

There are some systems on the market to detect objects falling into a swimming pool but they work on motion and a splash and subsequent wave must be present for the alarm to be triggered.

The acoustic signature system of this invention will work without splash, wave, or any form of mechanical movement. The ROM could be programmed for an animal (e.g., dog, cat, etc.) but an inanimate subject will not trigger it (e.g., rock, corpse). However, an unconscious human would be detected.

DESCRIPTION OF THE DRAWINGS:

The above and other objects, advantages and features of the invention will become more apparent when considered with the following specification and accompanying drawings wherein.

DETAILED DESCRIPTION OF THE INVENTION

The non-invasive diagnostic apparatus and method disclosed and claimed in my above-identified application is performed using a vessel or container 10 which is of sufficient size to at least hold a portion of a human body therein such that the portion can be voluntarily articulated by the human without engaging or contacting the sidewalls. In the illustrated embodiment, the vessel 10 is a large tank in which a human H is immersed up to the neck line. In a preferred embodiment, the sidewalls S1, S2, S3 and S4 and bottom are preferably formed of or coated with an acoustic absorber AB so that there are substantially no reflections of acoustic energy from the sidewalls and that any acoustic energy launched by the human H body, or body parts, are received directly by one or more hydrophones T1, T2 . . . TN, which are oriented to face the human'body. (While in this embodiment, the specimen or patient is a human, it will be appreciated that the same techniques may be used in connection with race horses, dogs, cats and other animals, but, in this preferred embodiment, the invention is particularly applicable to diagnostic purposes for use with humans).

Figure 2:
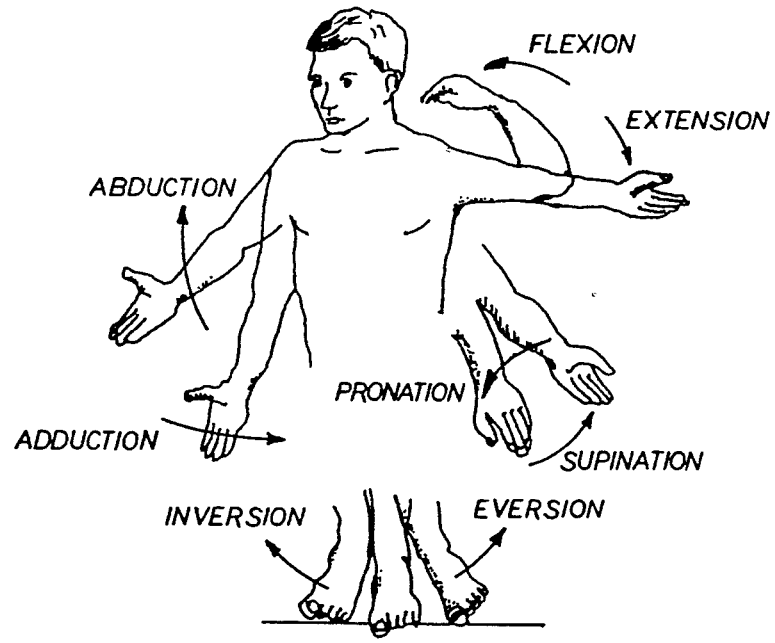
FIG. 2 is a diagrammatic illustration of a few movements of the body at the joints (from Wedding et al. "Medical Terminology", copyright 1988)

Various movements made by the body at the joints are illustrated in FIG. 2 and these generate sounds. Sounds emitted from the human body caused by movements of the skeletal portion (skeletal sounds) and/or blood flow (cardiovascular sounds) and/or air flow (respiratory) are detectable using the invention.

Noises made by the flow of blood in the human cardiovascular system and skeletal noises in the joints of a human skeleton and respiratory noises provide a wide variety of sounds (mostly infrasonic) which, when the human body is partially or completely immersed in a body of an acoustically transmissive liquid medium ATL such as water, vegetable oil, etc., are directly coupled to the liquid medium and thus launched into the liquid medium. Infrasonic levels are particularly well coupled to the ATL and thence to a transducer. Each joint, for example, has a unique acoustic signature. Joints which are injured or diseased can have their own unique acoustic signatures or sounds they make which are launched into the liquid medium. Thus, each individual skeletal system make or produces a unique pattern of sonic energy or noise which are normally infrasonic or but, when immersed in a body of acoustically transmissive liquid such as water, vegetable oil and the like, can be detected by hydrophones or underwater microphones T1, T2 . . . TN.

The invention has use in locating missing or lost divers, surveillance of bodies of water for surreptitious entry to the body of water by humans, and, as discussed extensively above, non-invasive medical diagnosis, both of skeletal, cardiovascular ailments, etc., as well as providing a baseline for future diagnosis.

Figure 1:
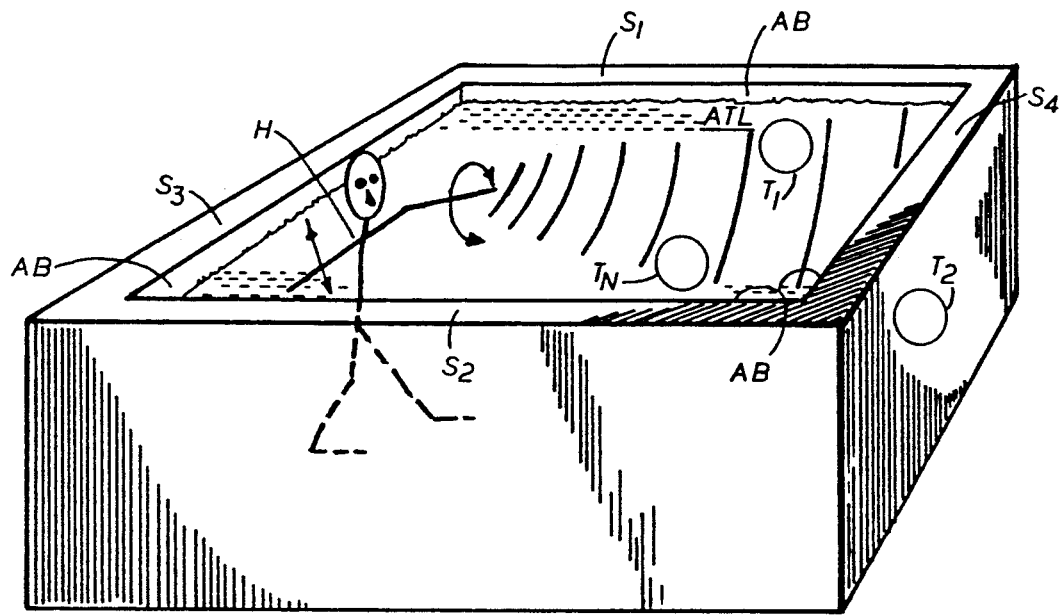
FIG. 1 is a perspective isometric view of a apparatus incorporating the invention.

In FIG. 1, the hydrophone or transducers T1, T2 . . . TN may comprise of one or a plurality of different microphones, and are each referred to herein as acoustic transducers and they convert acoustic energy transmitted in the body of acoustically transmissive liquid ATL.

Figure 3:
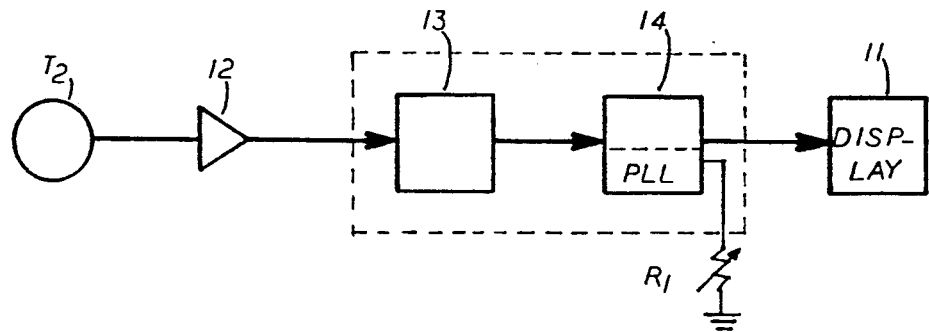
FIG. 3 is a block diagram thereof.

Acoustic transducers T may be positioned in the body of acoustically transmissive liquid ATL or a wall of vessel 10 and converts all sonic energy to electrical signals. As shown in the block diagram of FIG. 3, the electrical signals produced by transducer T2 are amplified by preamplifier 12 and supplied to a bandpass filter 13, the output of which is supplied to a discriminator 14 and then to a display or recorder 11. The bandpass filter removes unwanted background noise and interference and passes the desired cardiovascular and/or skeletal sounds. The configuration of the filter is in a cascaded high-pass/low-pass configuration to maximize attenuation outside the desired frequency. While there are some sounds that are in the audible range, typical sounds made by the movement of the human skeletal system are in the subsonic or infrasonic range and thus in the preferred embodiment, the bandpass filter is designed to restrict frequencies to this. Moreover, the solid state discriminators include a phase lock loop PLL which is adjustable or programmed by adjustable resistor R1 to pass a predetermined discrete pattern of electrical signals constituting a sonic profile, signature or imprint of the movement of a selected body part. For example, the up and down sidewise movement (abduction-adduction) of the human arms shown in FIG. 1 is movement of the humerus bone or upper arm bone in the shoulder, movement of the fibial relative to the femur e.g., the knee joint, provides subsonic sounds (apart from the audible snapping of joints) which are unique and distinctive.

Figure 4:
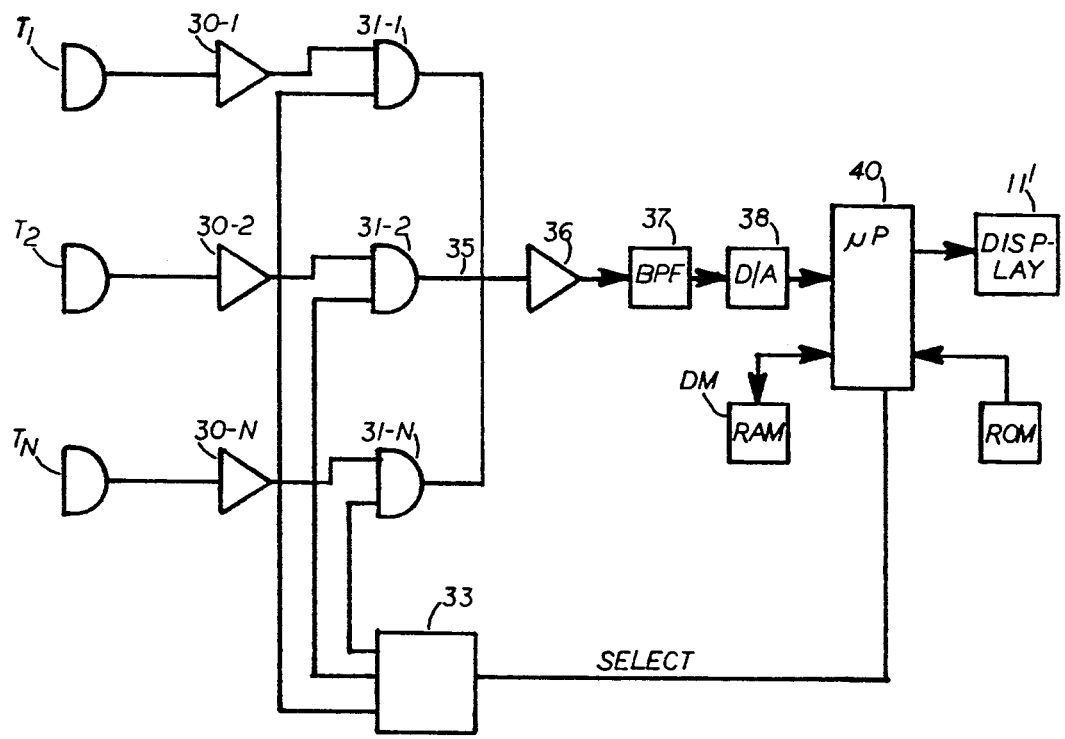
FIG. 4 is a detailed block diagram.

Referring now to the embodiment shown in FIG. 4, a plurality of transducers T1, T2 . . . TN are amplified in preamplifiers 30-1, 30-2 . . . 30-N. While the multiplexing operation can be performed either at the transducer head or in an electronic's compartment, in this embodiment, the multiplexing operation is performed at the transducer head. In this case, the gates 31-1, 31-2 . . . 31-N receive gate signals from counter 33 via line "select". The gated analog signals are coupled by a coaxial cable 25 to an amplifier 36, bandpass filter 37BPF and analog-to-digital converter 38. The digital signals constituting the multiplexed output for the individual transducers are then supplied to the microprocessor 40 which controls the "select" line and, in turn, the counter 33.

In this case, the microprocessor 40 performs the filter and discriminator functions discussed earlier, identify and classify the acoustic signatures from the different body systems, and also operates the display 71 which may be a CRT, LCD, plasma, display.

In addition, a read-only memory ROM is provided for storing sonic profiles of large number of joints or cardiovascular flow in particular parts of the body which is used to compare with the incoming acoustic or sonic profiles so as to identify the sounds and the cardiovascular or skeletal from which they emanate. At the same time, microprocessor 40 stores for short term use data in a random access memory DM.

The entire spectrum of sonic signals for each joint in the skeletal system or the cardiovascular system and each part of the body may be detected, digitized and stored in a computer memory. For this purpose, a digital-to-analog converter DA is provided for converting each acoustic signature to a digital signal and processed by microprocessor MP and stored in a digital memory DM. Moreover, each acoustic signature may be analyzed and compared with a standard acoustic signature which has been derived from analysis of a large number of acoustic signatures. For example, a large number of individuals may be placed in vessel 10, and asked to move a particular part of their body in a particular fashion. For example, the human H shown in FIG. 1 is asked to point his right arm directly outwardly from the side and then move it in an arc up and down (while the shoulder joint is, of course, below the surface of the acoustically transmissive liquid ATL). See FIG. 2 for a sample of the various movements. A large number of individuals are asked to do the same articulation of their right arm. The acoustically recorded signatures for each individual are then analyzed to establish a norm or "standard" which may be stored in a read only memory ROM, along with other fixed program files. The standard may be according to age, sex, physical size (e.g., skeletal size). As another example, a group of individuals may each be asked individually to insert their leg into the acoustic transmissive liquid ATL and hold it stationary and the transducer 11 used to detect the infra subsonic signals made by the coursing of the blood flow through the cardiovascular system and thereby derive an acoustic signature to establish as a standard comparison. In like manner, individuals having a particular ailment may be asked to immerse a part of their body into the acoustically transmissive liquid and those known ailments then utilized as a base for establishing a characteristic departure from the standard. Numerous other examples of similar character may be given but it is believed that the above is sufficient to establish the broad implication and applications of the invention.

Since the acoustic signatures for different skeletal areas and parts of the human and flows in different parts of the cardiovascular system have their own characteristic acoustic signatures, transducers may constituted by a plurality of hydrophones T1, T2 . . . TN for example, and bandpass filters, one utilized for example, for selected cardiovascular signals and one used for selected skeletal signals. Large numbers of individual channels may be utilized, each attuned to a particular skeletal sound or a particular cardiovascular sound. Finally, different combinations of skeletal and cardiovascular sounds may be utilized to detect and identify a particular individual or to detect and identify particular ailments and/or symptoms of ailments.

THE PRESENT INVENTION

Figure 5:
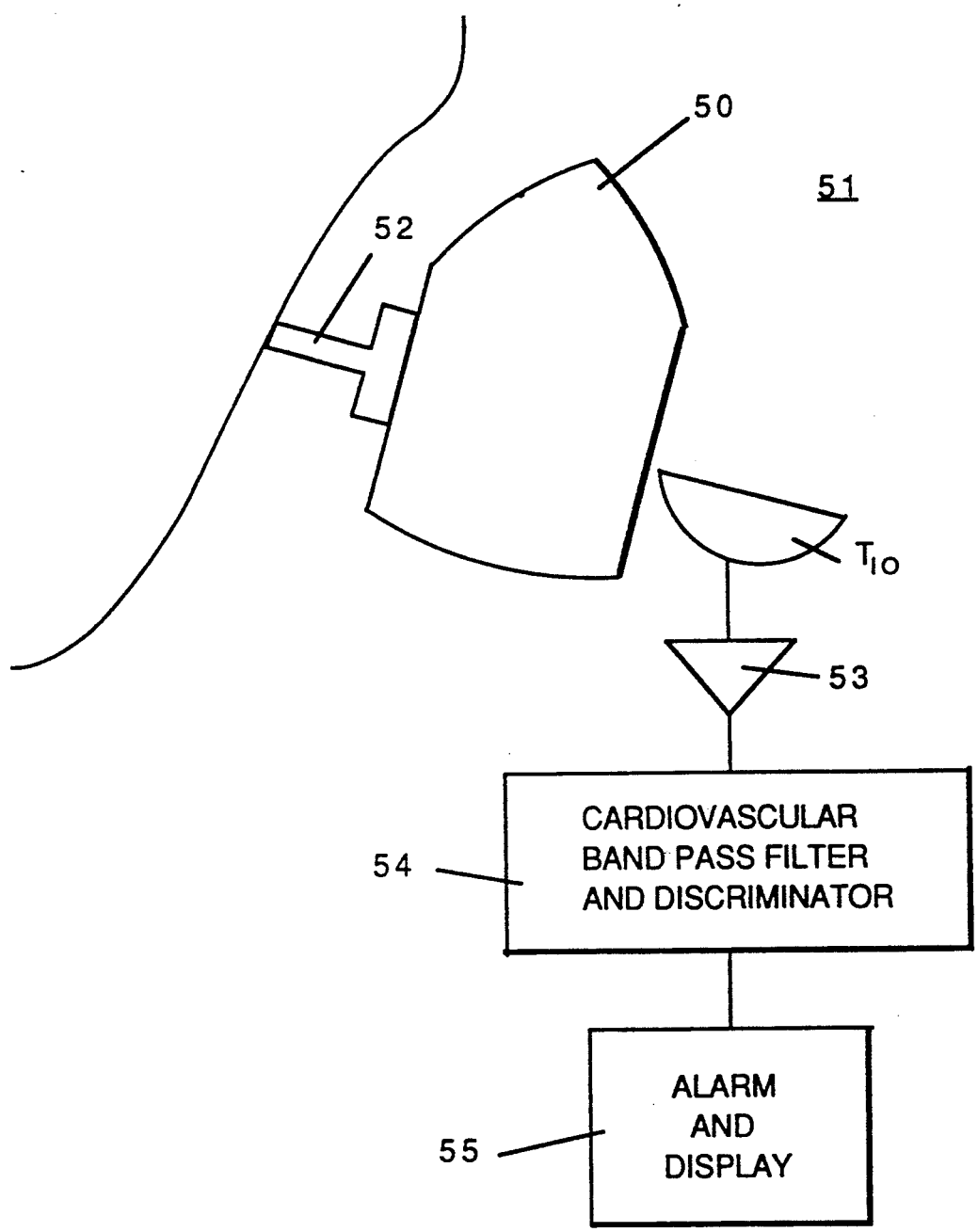
FIG. 5 is a simplified block diagram of an intrusion detection system incorporating the invention.

Referring to FIG. 5, a ship 50 floats in a body of water 51 at a dock 52 and it is desired to detect unauthorized entry into the body of water by an intruder. A transducer or hydrophone $T_{1D}$ is immersed in the body of water 51 to convert all underwater pressure waves to electrical signals which are amplified by an amplifier 53. The amplified signals are supplied to cardiovascular bandpass filter and discriminator 54. Bandpass filter and discriminator 54 removes unwanted background noises and interference and passes signals in the range of those generated by the human cardiovascular system (e.g., infrasonic to about 600 Hz). The discriminator portion of element 54 is programmed to detect the human acoustic signature in contrast to non-human other animals having a cardiovascular system which may also be in the area of the body of water to be protected. When cardiovascular bandpass filter and discriminator 54 detects a human cardiovascular sonic profile, it activates alarm 55 to thereby apprise the operator of the entry to the protected body of water 51 by unauthorized animals or personnel. Alarm 55 may be a signal light display.

The transducer $T_{1D}$ may be physically rotated about its axis to scan the protected body of water and thus obtain angular directional information regarding the intruder. Alternatively, a plurality of transducers dispersed in an arc or circle may be scanned electronically to obtain directional information and electronic scanning of the protected area can be effected using scanning circuitry of the type shown in FIG. 3 of my application Ser. No. 07/545,954, incorporated herein by reference. Instead of detecting selected fish, or other aquatic animals, the discriminator is programmed to detect sounds of various human anatomy systems. In addition, range and depth of the intruder can be determined using the same range and depth detection principles and apparatus as disclosed in my application Ser. No. 07/545,954.

Figure 6:
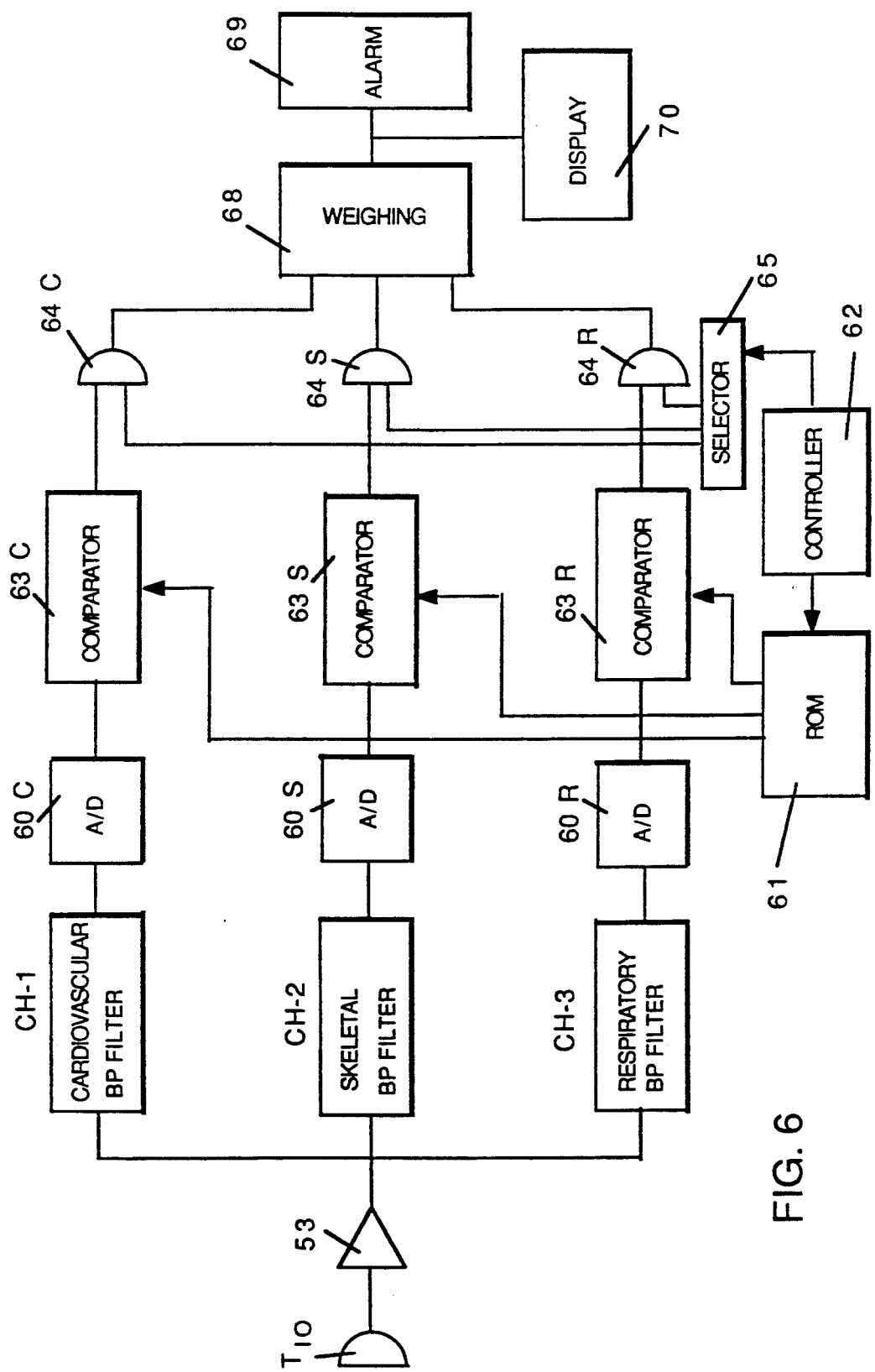
FIG. 6 is a detailed block diagram of an intrusion detection system incorporating the invention.

Referring now to FIG. 6, a further embodiment of the invention utilizes three channels, one channel CH1 for the cardiovascular sounds, one channel CH2 for the sounds of the skeletal system, and one channel CH3 for sounds of the respiratory system. In this embodiment signals from amplifier 53' are applied to the three channels Ch1, Ch2 and CH3, converted to digital signals by A/D converter 60C, 60S and 60R.

A read-only memory (ROM) 61 stores sonic profiles of:
1) human cardiovascular system sounds,
2) human skeletal sounds, and
3) human respiratory system.

A controller 62 causes these sonic signatures or profiles to be supplied to each of the channel comparators 63C, 63S and 63R. The outputs of each of the comparators 63C, 63S and 63R are gated through AND gates 64C, 64S and 64R by selector 65, which is also connected to controller 62. Selector 65, in conjunction with gates 64C, 64S and 64R can serve to multiplex the chanel signals to weighting unit 68. As noted earlier, the presence of cardiovascular sounds in humans is invariable and are launched into the water, even when a diver is in a heavy rubber wet suit (which may attenuate some of the sound of loosely fitting with attenuating air spaces). The carotoid arteries in the neck convey blood from the aorta to the head and blood flow in these arteries launch sound almost directly into the water. Hence, the cardiovascular sonic profile must be present and weighting unit 68 assigns the highest weight (100) to the presence of this signal in its channel. Human respiratory sounds can be similar to many sea creature sounds and thus, the presence of an output in channel CH3 is given a lower weight by weighting unit 68 and is used to reinforce or add to a positive detection identification of an intruder into the protected body of water. Similarly, since musculo-skeletal sounds are diminished significantly if the intruder is not moving, or is moving slowly, or is propelled or pulled by some underwater propulsion device, output of the skeletal channel CH2, while generally unique, is used to reinforce or add to a positive detection identification of an intruder into the protected body of water. The presence of the human cardiovascular sonic profile and absence of skeletal sounds and the presence of human respiratory sound profile or signature can be a sign of unauthorized intrusion by a scuba diver using tide or current flow or some propulsion device to enter the protected area, for example. It can also be used to indicate an authorized scuba diver who may be passed out or in trouble, for example.

If a swimming pool is being protected, the ROM can be programmed to detect an infant or child or dog, cat, etc., getting into the pool. Moreover, while swimming alone is not safe, the device can be installed to detect if the swimmer is not swimming by detecting the absence, over a predetermined time interval, of the human musculo-skeletal sonic profile.

An alarm 69 and a flashing light display 70 can be activated upon detection of an unauthorized intrusion.

Moreover, if a plurality of transducers are oriented to cover the prescribed body of water, scanning of the transducers to detect the source of the strongest cardiovascular signal provides direction which can be displayed on display 70. Finally, if there are authorized personnel in the water, their location should be known in advance, or each provided with a sounding device which can be used to identify them in a fashion similar to IFF principles.

Figure 7:
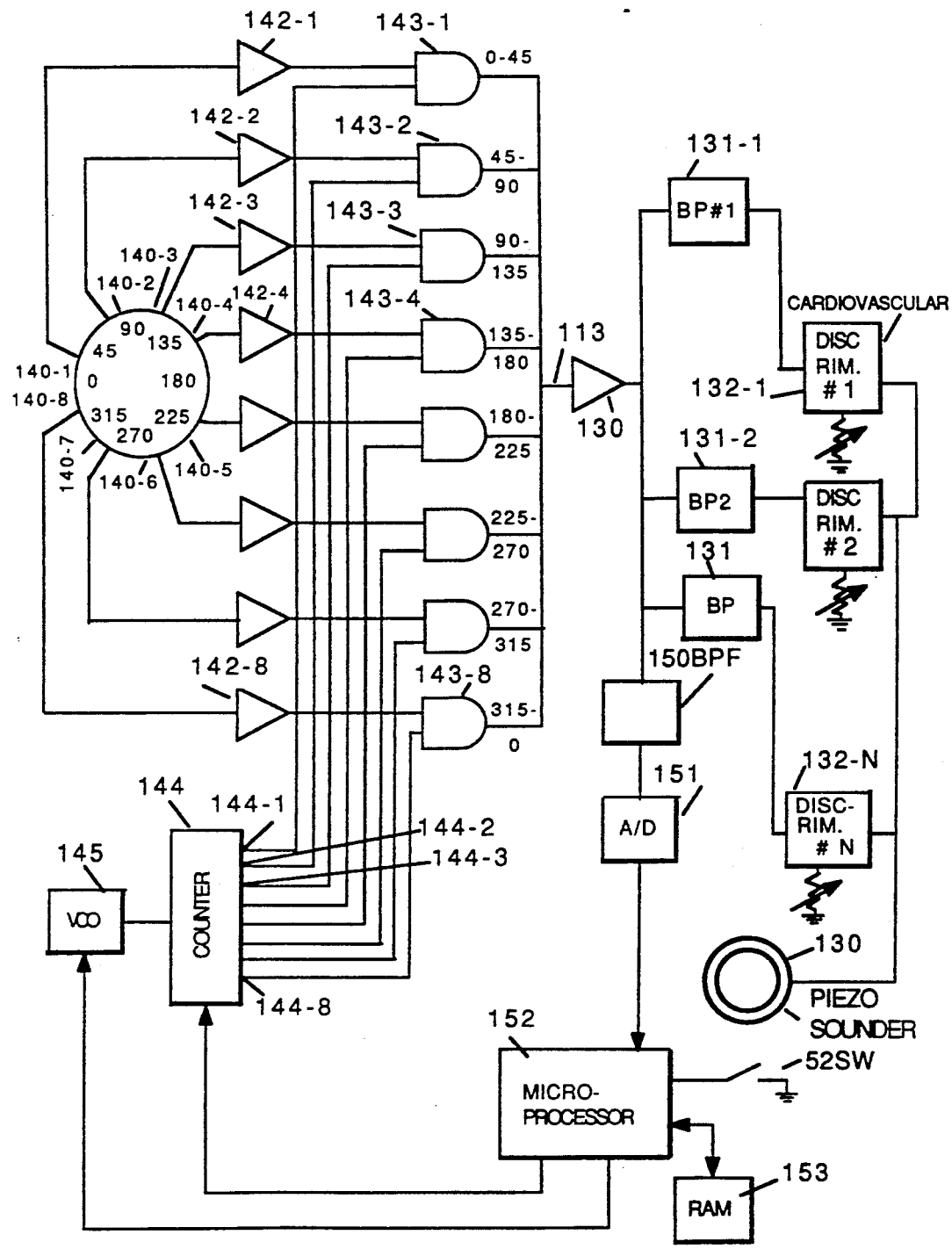
FIGS. 7 and 8 are block diagrams of further embodiments of the invention.

Instead of scanning for target aquatic animals TF by mechanical rotation of transducer T1D, FIG. 7 illustrates an electrical scanning wherein there are two transducers per quadrant making a total of eight transducers, there can be, of course, be more or less transducers as desired. Each transducer 140-1, 140-2, 140-3 . . . 140-8 is connected to a preamplifier 142-1, 142-2, 142-3 . . . 142-8, respectively, whose outputs are supplied to a gate circuit 143-1, 143-2 . . . 143-8, respectively, which receive as a second input enable or gate signals from a counter 144 which, in turn, receives inputs from control oscillator 145. The arrangement is such that the oscillator 145 supplies pulses to counter 144 which counts these pulses to produce outputs on terminals 144-1, 144-2, 144-3 . . . 144-8, one for each gate circuit 143-1 so that these pulses in effect sample or select the signals picked up by each of the transducers 140-1, 140-2, 140-3 . . . 140-8. They thus appear on the outputs of gates 143-1, 143-2 . . . 143-8 as the acoustic signals detected for the eight quadrant segments 0 to 45 degrees, 45 to 90 degrees, 90 to 135 degrees, 135 to 180 degrees, 180 to 225 degrees, 225 to 270 degrees, 270 to 315 degrees and 315 to 0 degrees. The time period for sampling e.g., the rate of the VCO operation 145 and the counter operation 144 can be adjusted, either speeded up or slowed down. A speed of 1 rpm, for example, results in each segment sampling of about 7.5 seconds. Each of the signals issuing from the gate circuits 143-1, 143-2 . . . 143-8 e.g., the multiplexed signals, are supplied by coaxial cable 113 to amplifier 150 and each of the signals is supplied to channels, bandpass filters 131-1 . . . 131-N, discriminators 132-1 . . . 132-N, one channel for each sonic profile in the system and then to a piezo-sounder 130.

The multiplexed signals from amplifier 150 are bandpass filtered in filter 50BPF and are supplied to analog-to-digital converter 151 which supplies these signals to microprocessor 152 which serves as a controller for counter 144 and voltage controlled oscillator 145. Bandpass filter 150 eliminates all periodic signals from machines, etc. and passes only cardiovascular biosound signals. Microprocessor or controller 152 detects the maximum cardiovascular sound amplitude in each segment of transducer 140-1, 140-2, 140-3 . . . 140-8 and stores same in memory 153 and causes counter 144 to terminate the scan to temporarily lock on those segments (there may, of course, be several intruders in the body of water) in which the maximum amplitude cardiovascular is being produced. For example, if the maximum amplitude of incoming biosound signals is between segments 40-3 and 40-4, indicating that there is human cardiovascular activity in the area between 90 and 180 degrees (these angular directions are relative of course), the microprocessor 152 will cause counter 144 to lock on and provide gate signals to gates 143-3 and 143-4. If the detected signals do not appear to be of interest, the processor 152 can be instructed to resume the scanning operation by signal switch 152SW.

It will be appreciated that as described in connection with FIG. 8, microprocessor 52 can be programmed to perform the functions of bandpass filters 31-1' and 31-2' as well as the functions of discriminators 32-1' and 32-2'.

The bandpass filtered signals from bandpass filters 31-1' and 31-2' are supplied to display drivers 53 and 54, respectively, which, in turn, drive displays 55 and 56, respectively. These displays can be the bar graph displays in which the angular orientation of the particular segment which is receiving a biosound signal is being displayed or can be LCD-type displays.

Referring again to the counter 144, the gate pulses therefrom to the gates 143-1, 143-2, 143-3 . . . 143-8 in effect cause a scanning of the sensor segments or transducer segments 140-1, 140-2, 140-3 . . . 140-8 and, in a preferred embodiment, the scan rate is at about 1 rpm. At this rate the gates will pass the transduced electric signals from the transducers 140 about every 7-½ seconds during the scan mode and then between one, two or three adjacent segments according to the output of the microprocessor 152. Thus, should the human cardiovascular sound be in a location between bridging two transducer segments, and then moves to where it is basically centered on one segment, the microprocessor tracks this movement and provides an indication on the display of the movement of the intruder and the direction of the movement of the intruder. For example, if the intruder is swimming in a circle around the transducer, the output of the different transducers will detect the cardiovascular acoustic signature transmitted by the intruder as he swims activating each transducer in turn and providing a visual display of the swimming movement.

The kinds of sounds generated by the intruder (cardiovascular, respiratory or skeletal) are detected by the discriminators which, as indicated above, in this preferred embodiment, are programmed to detect sounds unique cardiovascular sounds of humans. A solid-state discriminator unit which has been found useful for this is designated as LM567 by National Semiconductor, but obviously the invention is not limited thereto.

Connections 132-1M and 132-2M from the discriminators to microprocessor 152 provides for logical detection.

Figure 8:
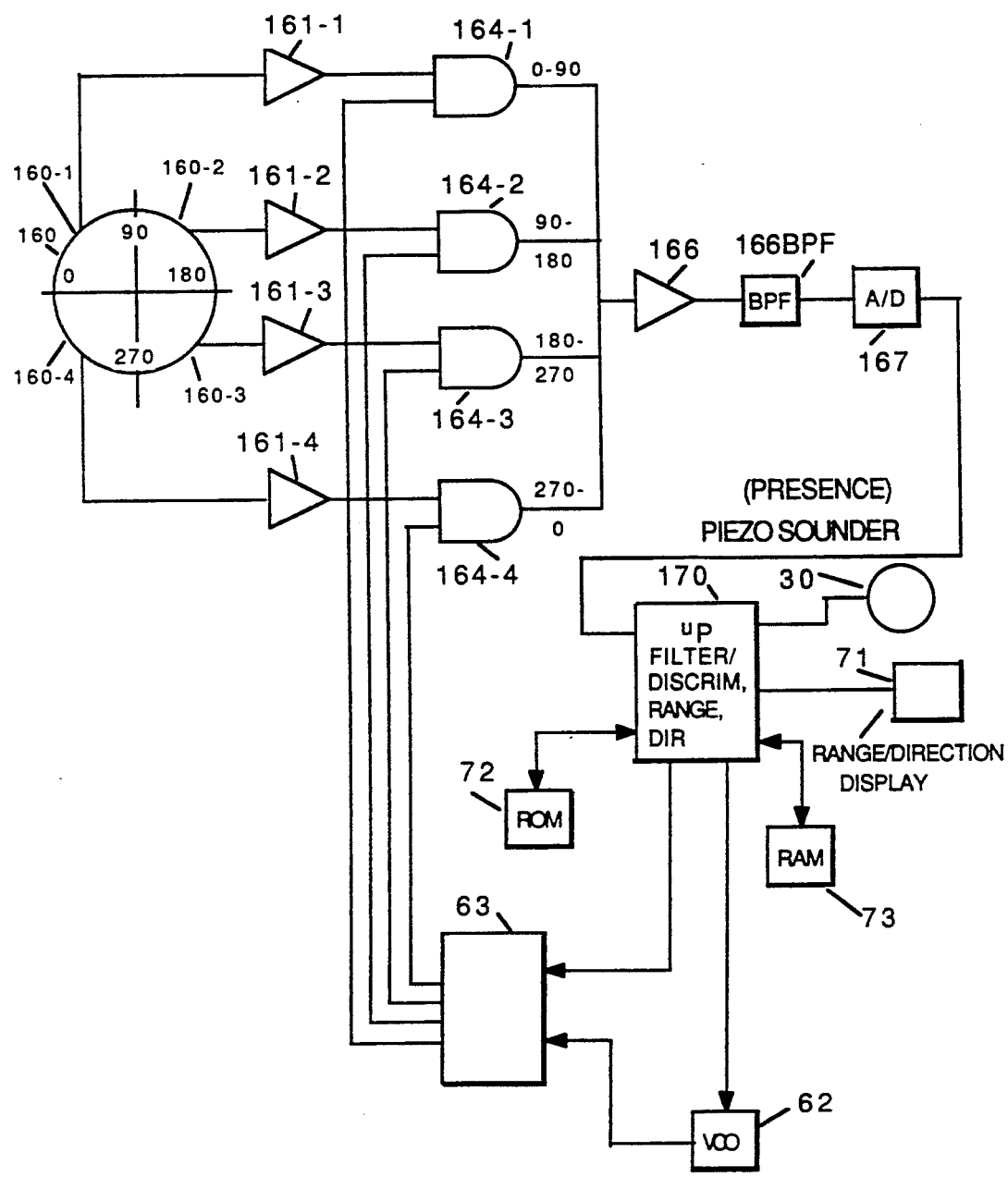

Referring now to the embodiment shown in FIG. 8, the transducer 160 has four segments 160-1, 160-2, 160-3 and 160-4 covering the 0 to 90 degree segment quadrant, 90 to 180 degree quadrant, 180 to 270 quadrant, and 270 to 0 degree quadrant. The signals from each of the quadrants are amplified in preamplifiers 161-1, 161-2, 161-3 and 161-4. While the multiplexing operation can be performed either at the transducer head or in the electronic's compartment, in this embodiment, the multiplexing operation is performed at the transducer head. So in this case, the gates 164-1, 164-2, 164-3 and 164-4 are located in the transducer head and receive gate signals from counter 163 via line 164. The gated analog signals constituting the 0 to 90 degree, 90 to 180 degree, 180 to 270 degree ad 270 to 0 degree segments are coupled by a coaxial cable 165 to an amplifier 166, bandpass filter 66BPF and analog-to-digital converter 167. The digital signals constituting the multiplexed output for the individual segments are then supplied to the microprocessor 170 which controls oscillator 162 and, in turn, the counter 163 in a manner similar to the control performed by microprocessor 152 in connection with the embodiment shown in FIG. 3.

In this case, the microprocessor 170 can perform the filter and discriminator functions discussed earlier herein and also operates the piezo-sounder 130 and the range and direction of display 171.

In addition, a read-only memory 72 is provided for storing sonic profiles of the cardiovascular, respiratory and skeletal systems of humans which is used to compare with the incoming acoustic or sonic profiles so as to identify a specific species of sound. At the same time, microprocessor 170 stores for short term use data in a random access memory 173 for making range calculations as described in my application Ser. No. 07/545,954, incorporated herein by reference. It is, of course, obvious, that the amplitudes of the sound are also used in this case to determine range. However, range determinations may also be computed from times of arrival of acoustic energy from a given acoustic target.

While in the preferred embodiment of the invention, a scanning action is performed, it will be appreciated that a separate channel can be provided for each transducer sector and the outputs of each discriminator 132 sampled or multiplexed to a common display which indicates the sector direction, range, depth of the intruder in a given sector.

While there has been shown and described a preferred embodiment of the invention, it will be appreciated that various other adaptations and modifications of the invention will be readily apparent to those skilled in the art and it is intended to encompass such obvious modifications and adaptations in the spirit and scope of the claims appended hereto.

What is claimed is:

1. A method of providing surveillance of a body of water to detect surreptitious intrusion thereto by humans comprising:
   immersing a sonic transducer in said body of water to convert sonic energy received thereby to electrical signals,
   passing said electrical signals through a bandpass filter having its passband in the infrasonic range to produce bandpass filtered signals in the infrasonic range, and passing electrical signals from said bandpass filter through a discriminator having a phase lock loop which is programmed to pass a discrete pattern of electrical signals constituting a sonic profile of the human cardiovascular system.

2. Apparatus for detecting the presence of one or more human or animal in a predetermined body of water, comprising:
   transducer means for converting sonic energy in said body of water to electrical signals,
   bandpass filter means tuned to pass electrical signals corresponding to sonic energy generated by blood flow in the cardiovascular system and launched into said predetermined body of water and connected to said transducer means,
   programmable discriminator means connected to said bandpass filter means and programmed to detect the electrical signals corresponding to sonic energy produced by blood flow in cardiovascular systems of said human or animal, and producing a presence signal upon detection of a human or animal, and
   alarm means for indicating the presence or absence of human or animal in said predetermined body of water by the presence or absence of said presence signal.

3. Apparatus as defined in claim 2 wherein said transducer means includes a plurality of transducers arranged in a pattern and including means for scanning said plurality of transducers to determine the direction, relative to said transducers of said human or animal.

4. Apparatus as defined in claim 3 including means to determine range to said human or animal solely from the sonic energy emitted by said human or animal.

5. Apparatus as defined in claim 2 including means for determining range to said human or animal solely from the sonic energy emitted by said human or animal.

6. Apparatus as defined in claim 2 including means to determine the depth of said human or animal in the water solely from the sonic energy emitted by said human or animal.

7. Apparatus for detecting the presence of one or more human or animal in a predetermined body of water, comprising:
   transducer means for converting sonic energy in said body of water to electrical signals,
   bandpass filter means tuned to pass sonic energy generated by a cardiovascular system and launched into said predetermined body of water and connected to said transducer means,
   programmable discriminator means connected to said bandpass filter means and programmed to detect the cardiovascular sonic systems of said human or animal, and producing a presence signal upon detection of a human or animal, and
   alarm means for indicating the presence or absence of human or animal in said predetermined body of water by the presence or absence of said presence signal and wherein said discriminator means includes means for converting signals from said bandpass filter means to digital signals, a comparator, a read-only memory having stored therein a sonic profile of sonic energy generated by cardiovascular systems of said humans or animals, and means for connecting said read-only memory to said comparator.

8. Apparatus for providing surveillance to a body of water, comprising:
   transducer means for converting sonic energy in said body of water to electrical signals,
   first channel means connected to said transducer for receiving said electrical signals and having a bandpass filter therein for overpassing signals in the range of human cardiovascular sonic signals,
   second channel means connected to said transducer for receiving said electrical signals and having a bandpass filter therein for only passing sonic signals in the range of human musculo-skeletal sonic signals,
   third channel means connected to said transducer for receiving said electrical signals and having a bandpass filter therein for only passing sonic signals in the range of human respiratory system sonic signals,
   means for storing sonic profiles of said human cardiovascular, musculo-skeletal and said respiratory system sonic signals, respectively,
   comparator means in each of said channels,
   means connecting said means for storing to each of said comparator means, respectively,
   weighting means connected to receive the outputs of each of said comparators, with the output of the comparator in said first channel being accorded the highest weight in determining the presence or absence of a human in said body of water, and
   means connected to said weighting means for indicating the presence or absence of a human in said body of water.

* * * * *